United States Patent [19]
Hsieh et al.

[11] Patent Number: 5,907,593
[45] Date of Patent: May 25, 1999

[54] IMAGE RECONSTRUCTION IN A CT FLUOROSCOPY SYSTEM

[75] Inventors: Jiang Hsieh, Brookfield, Wis.; Stephen W. Metz, Paris, France; Girish Saligram, Waukesha, Wis.; Guy M. Besson, Wauwatosa, Wis.; Hui Hu, Waukesha, Wis.; Sandeep Dutta, New Berlin, Wis.; Robert F. Senzig, Germantown, Wis.; Min Xie, Waukesha, Wis.

[73] Assignee: General Electric Company, Milwaukee, Wis.

[21] Appl. No.: 08/978,802

[22] Filed: Nov. 26, 1997

[51] Int. Cl.$^6$ ........................................ A61B 6/03
[52] U.S. Cl. ........................................ 378/4; 378/901
[58] Field of Search .................... 378/4, 15, 901

[56] References Cited

U.S. PATENT DOCUMENTS 5,375,156   12/1994   Kuo-Petravic et al. ............ 378/9

*Primary Examiner*—David Vernon Bruce
*Attorney, Agent, or Firm*—John S. Beulick; Christian G. Cabou; Phyllis Y. Price

[57] ABSTRACT

A CT Fluoro system having an architecture and algorithms which facilitate increasing the frame rate and providing acceptable image quality is described. Generally, and in one embodiment, the system includes apparatus and algorithms that speed-up image reconstruction and reduce image artifacts that may result from such fast reconstruction. The fast reconstruction is achieved by performing, for example, view compression, channel compression, backprojection with reduced delay, and parallel processing.

25 Claims, 2 Drawing Sheets

IMAGE RECONSTRUCTION IN A CT FLUOROSCOPY SYSTEM

FIELD OF THE INVENTION

This invention relates generally to computed tomography (CT) imaging and more particularly, to image reconstruction in a CT fluoroscopic system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighting ("HW") algorithms which weight the collected data as a function of view angle and detector channel index. Specifically, prior to filtered back projection, the data is weighted according to a helical weighting factor, which is a function of both the view angle and detector angle. As with underscan weighting, in a HW algorithm, projection data is filtered, weighted, and backprojected to generate each image.

In CT fluoroscopic systems ("CT Fluoro"), data collected from a helical scan may be utilized to generate sequential frames of images to help, for example, in guiding a needle to a desired location within a patient. A frame, like a view, corresponds to a two dimensional slice taken through the imaged object. Particularly, projection data is processed at a frame rate to construct an image frame of the object.

With known CT Fluoro systems, the general objective is to increase the frame rate while minimizing image degradation. Increasing the frame rate provides many advantages including, for example, that an operator physician is provided with more timely (or more up to date) information regarding the location of a biopsy needle. Typically, however, increasing the frame rate is at odds with minimizing image degradation. For example, the more often projection data is filtered, weighted and backprojected, the slower the frame rate. The frame rate is thus limited to the computational capabilities of the CT Fluoro system.

It would be desirable to provide a CT Fluoro system that has an increased frame rate without significantly adversely affecting image quality.

SUMMARY OF THE INVENTION

These and other objects may be attained by a CT Fluoro system having an architecture and algorithms which facilitate increasing the frame rate and providing acceptable image quality as described below. Generally, and in one embodiment, the system includes apparatus and algorithms that speed-up image reconstruction and reduce image artifacts that may result from such fast reconstruction. The fast reconstruction is achieved by performing, for example, view compression, channel compression, backprojection with reduced delay, and parallel processing.

More particularly, and with respect to an exemplary embodiment of view compression, every even view in the compressed data set contains unmodified projection data in the original data set, and every odd view in the compressed data set contains an average of the two views in the original data set. Specifically, the new projection data set is generated in accordance with:

$$p_{compressed}(k) = \begin{cases} p_{original}\left(\frac{3k}{2}\right) & k = 0, 2, 4, \ldots \\ 0.5\left[p_{original}\left(\frac{3k-1}{2}\right) + p_{original}\left(\frac{3k+1}{2}\right)\right] & k = 1, 3, 5, \ldots \end{cases} \quad (1)$$

Different kernels can, of course, be used in the compression process. Denoting $\Delta\theta$ as the angular increment in the original data set, the angular increment in the new data set is $3\Delta\theta/2$. Using the above described algorithm, the number of views used in reconstruction is only $2/3$ the number of original views.

To combating aliasing artifacts, the views can be expanded. Particularly, reducing the number of views used in the reconstruction process results in view aliasing artifacts in the reconstructed image. To reduce the aliasing artifacts, additional view data is generated and utilized in the backprojection process. More particularly, if $p_\beta(\gamma)$ represents the filtered version of the projection data set, the standard filtered backprojection algorithm backprojects $p_\beta(\gamma)$ from the gantry angles $\beta$. In accordance with the present reconstruction algorithm, a second set of filtered projection data is generated for a second set of gantry angles which bisect the first set of gantry angles $\beta$. Simple linear interpolation can be used, for example, to compute the second set of filtered projection data from the first set of data $p_\beta(\gamma)$. Both sets of data, i.e., the actual data and the generated data, at the corresponding gantry angles are then backprojected, and the image is reconstructed using such data.

Further, and with respect to performing channel compression, each projection channel is formed by two detector channels or cells. Particularly, the cells are ganged so that the ganged cells generate one output, or projection channel. The operation can be described by the following equation.

$$\xi'_k = \xi_{2k} + \xi_{2k+1} \quad (2)$$

The channel ganging can be performed, for example, immediately after air-calibration (Air-cal) correction.

The double channel ganging reduces spatial resolution. To at least partially compensate for the loss of resolution, a reconstruction filter kernel boost can be utilized. Particularly, the reconstruction filter (in frequency domain) is multiplied by the following window function:

$$\omega = 1 + \alpha_1 f + \alpha_2 f^2 + \alpha_3 f^3 + \alpha_4 f^4 \quad (3)$$

where $\alpha_1$ to $\alpha_4$ are parameters. In one specific embodiment, the parameter set of $\alpha_1=0.0$, $\alpha_2=0.6$, $\alpha_3=0.2$, and $\alpha_4=0.0$ is utilized.

To reduce patient motion artifacts, overscan weights are utilized. Since the overscan weight is constant along the channel direction, the filtering operation and weighting operation can be reversed and only one filtering per projection is needed. Each filtered projection can then be multiplied by different weights prior to the backprojection. The overscan weighting algorithm is performed in accordance with the following.

$$\omega(\gamma,\beta) = 3\theta^2(\gamma,\beta) - 2\theta^3(\gamma,\beta) \quad (4)$$

where $$\theta(\gamma,\beta) = \begin{cases} \dfrac{\beta}{\beta_o} & 0 \le \beta < \beta_o \\ 1 & \beta_o \le \beta < 2\pi \\ \dfrac{2\pi + \beta_o - \beta}{\beta_o} & 2\pi \le \beta < 2\pi + \beta_o \end{cases}$$

where $\beta_o$ is a parameter which specifies the overscan angle. The parameter $\beta_o$ is determined based on a compromise between image quality and reconstruction speed.

Also, and with respect to backprojection, for example, six different images are under reconstruction at any time, and multiple weighted projections are needed for these images. Of course, more (e.g., eight) or fewer images could be under reconstruction. Particularly, and in an exemplary system, for every 1/6th of the overscan rotation, a complete image is generated at one location. The backprojector memory therefore is divided into 6 sub-regions. At each time instance, a filtered projection is weighted with different weights and backprojected into all six sub-regions. Further, in the exemplary system, the reconstruction board is divided into 8 parallel pipes and since 6 images/overscan rotations are generated, the number of views used for each image generation needs to be divisible by 48 (i.e., 6 times 8). Therefore, and rather than starting each image at the multiple of 116 views, the second image is started at view 120, the third image starts 112 views after the second image, the fourth image starts again 120 views later, and the fifth image is further delayed by 112 views. This process continuous. The above described backprojection algorithm avoids significant penalties on either system delay or image artifacts.

To further speed-up the reconstruction process, many processes can be performed on different processors in parallel. For example, the pre-processing, filtering, backprojection, and post-processing can each be performed on different processors. With such a configuration, and while one processor is processing view i, a different processor can process view i+1. Further, while the backprojector is processing image number i, the post-processing unit can process image number i-1.

DETAILED DESCRIPTION

Figure 1:
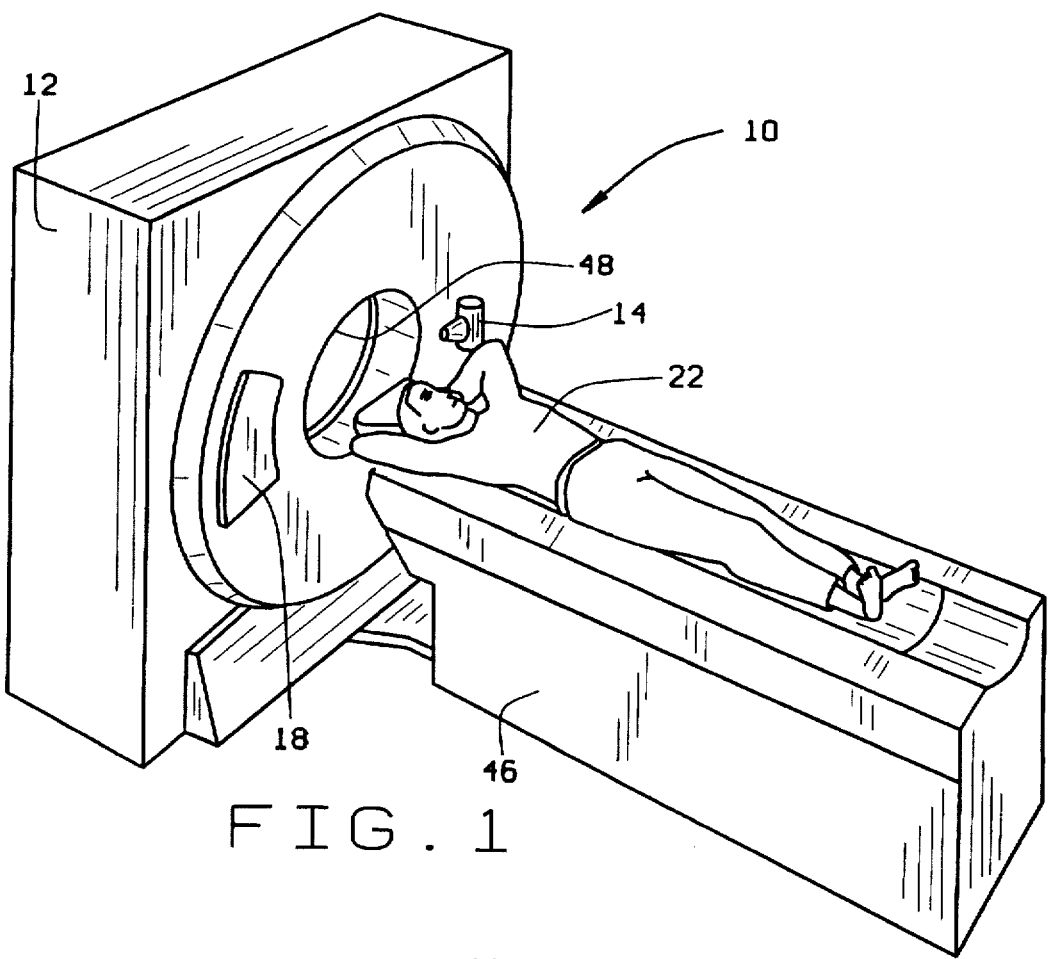
FIG. 1 is a pictorial view of a CT imaging system.
Figure 2:
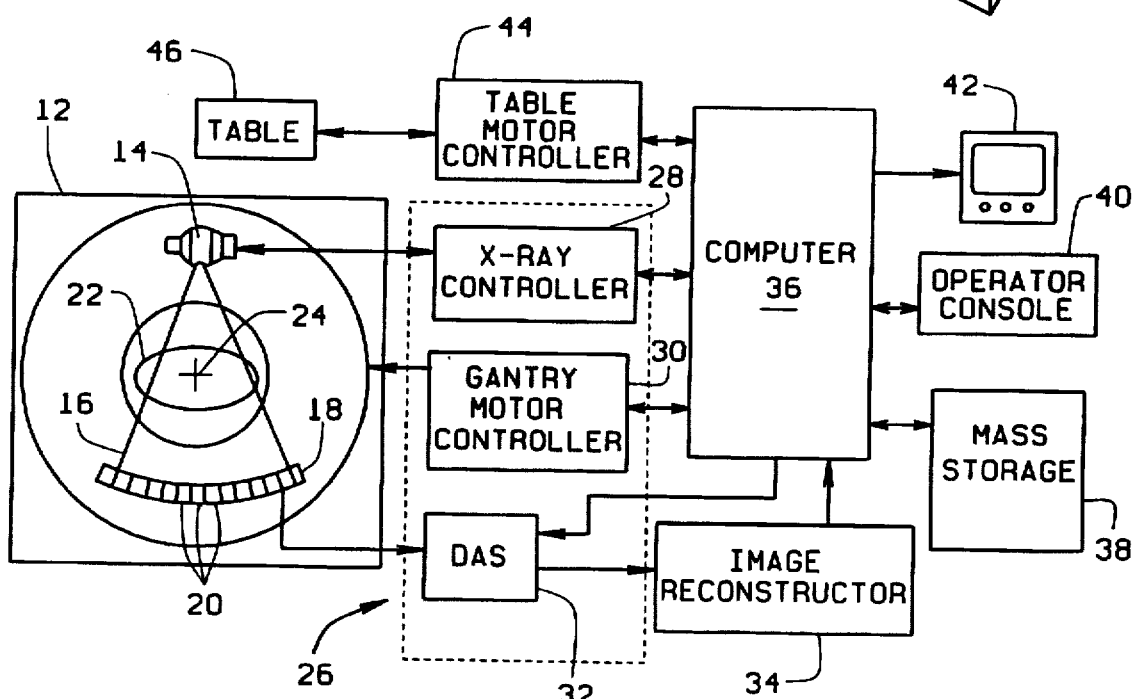
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on, i.e., dependent upon, both the fan angle and view angle. While the HE and HI algorithms provides generally acceptable image quality, such algorithms employ significant computational redundancies, and require significant hardware costs when reconstruction speed is crucial. For example, almost all projections that are used to generate an original image will have to be re-weighted, re-filtered, and re-backprojected to generate a new image that is even a small fraction of the rotation apart. Particularly, even where a significant amount of overlap occurs in projections of sequential images, to generate n images per gantry rotation, n times the amount of computation that is needed to generate a single image is needed during the gantry rotation.

The following discussion describes various apparatus and algorithms that can be used to speed-up image reconstruction or provide enhanced image quality in a CT Fluoro system. The apparatus and algorithms can be used by themselves or together in any combination. Further, although the apparatus and algorithms are sometimes described in the context of CT Fluoro, such apparatus and algorithms could also be used in other systems such as CT interventional systems. Generally, the discussion is separated into sections addressing view compression and expansion, channel compression with filter kernel boost, filtering, backprojection, and parallel processing.

A. View Compression and Expansion

To reduce the amount of data to be processed, a selective view compression algorithm can be utilized. Of course, reducing the amount of data to be processed provides the advantage of decreasing the amount of time required to generate an image during a fluoro scan. For example, one known CT system uses 984 views for image generation to avoid aliasing artifacts. The time taken for the tomographic reconstruction is directly proportional to the number of views used and therefore, by reducing the number of views used in image generation, the reconstruction can be sped up. The image quality should, of course, be maintained at an acceptable level.

More particularly, in an exemplary embodiment, the objective is to generate multiple images in as short a time as possible. To accomplish this objective, the images are reconstructed only with standard algorithms in a 256 by 256 matrix (i.e., no specialized processing is performed) and slight image quality degradation is acceptable, particularly since the main purpose for displaying the images is to guide the insertion of the biopsy needles.

Generally, with view compression, the view angle increment in the new data set preferably remains a constant. That is, the angles between the compressed views are the same throughout the entire data set. By maintaining the view angle increment constant, the reconstruction process is simpler and also is believed to be optimal for reducing aliasing artifacts since the view aliasing is determined by the largest angular spacing between views, not the average. Therefore, the compression algorithm preferably maintains the view angle increment constant.

The following algorithm satisfies the above described property, i.e., maintaining the view angle increment constant. More specifically, and in an exemplary embodiment, every even view in the compressed data contains unmodified projection in the original data set, and every odd view in the compressed data set consists of the average of the two views in the original data set. The new projection data set is generated in accordance with the following:

$$P_{compressed}(k) = \begin{cases} P_{original}\left(\frac{3k}{2}\right) & k = 0, 2, 4, \ldots \\ 0.5\left[P_{original}\left(\frac{3k-1}{2}\right) + P_{original}\left(\frac{3k+1}{2}\right)\right] & k = 1, 3, 5, \ldots \end{cases} \quad (1)$$

Different kernels can, of course, be used in the compression process. The simple average described above is only for the ease of illustration. In addition, the even or odd views in the equation are interchangeable, i.e., the odd views could be unmodified and the even views could be averaged.

With $\Delta\theta$ denoted as the angular increment in the original data set, the angular increment in the new data set is $3\Delta\theta/2$. Therefore, using the above described algorithm, the number of views used in reconstruction is only ⅔ the number of original views. For example, if the original data contains 984 views for $2\pi$ rotation, the new data set has 656 views per $2\pi$ rotation, which is a 33.3% reduction.

The following discussion relates to combating aliasing artifacts by expanding the views. Particularly, reducing the number of views used in the reconstruction process results in view aliasing artifacts in the reconstructed image. To reduce the aliasing artifacts, the present algorithm may be utilize to generate additional view data that can be utilized in the backprojection process to reduce aliasing artifacts.

Figure 3:
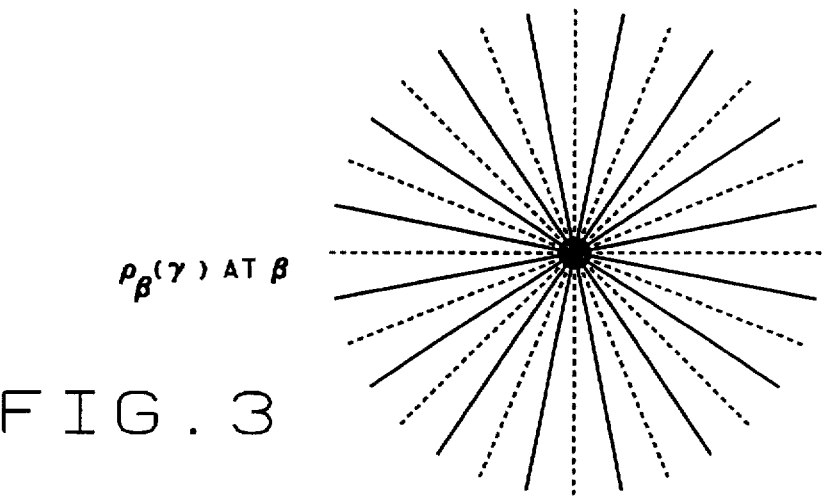
FIG. 3 is a graphical illustration of actual projection data and generated projection data used in connection with reducing aliasing artifacts.

More particularly, the present reconstruction algorithm differs from standard filtered backprojection algorithms only in the backprojection step, and the difference is graphically illustrated in FIG. 3 where the solid lines indicate the set of gantry angles $\beta$ at which a set of projection data is physically collected. For the purposes of the following discussion, $P_\beta(\gamma)$ represents the filtered version of the projection data set. The standard filtered backprojection algorithm backprojects $P_\beta(\gamma)$ from the gantry angles $\beta$.

In accordance with the present reconstruction algorithm, a second set of filtered projection data is generated for a second set of gantry angles, illustrated as dashed lines in FIG. 3 which bisect the first set of gantry angles $\beta$. Simple linear interpolation can be used, for example, to compute the second set of filtered projection data from the first set of data $P_\beta(\gamma)$.

Both sets of data, i.e., the actual data and the generated data, at the corresponding gantry angles are then backprojected, and the image is reconstructed using such data. The backprojection can be implemented, for example, on an image generation (IG) board in a pipe-line fashion to increase reconstruction speed. Of course, more views can be used for higher order interpolation. Also, more than two views can be generated between views.

The above described algorithm degrades the azimuthal resolution of the image. When other azimuthal-resolution limiting factors, such as the detector primary speed, are considered, the additional degradation may be unnoticeable or acceptable.

B. Channel Compression with Filter Kernel Boost

For computational speed-up, each projection channel may be formed by two detector channels or cells. Particularly, the cells are ganged, e.g., double ganged, so that the ganged cells generate one output, or projection channel. In the exemplary embodiment described below, it is assumed that the cells are double ganged. However, a higher compression ratio can be used. The ganging is described as follows:

$$\xi'_k = \xi_{2k} + \xi_{2k+1} \quad (2)$$

The channel ganging can be performed, for example, immediately after air-calibration (Air-cal) correction. As is known in the art, the Air-cal correction includes normalization, channel expansion, Qcal (i.e., image calibration), theta fix, and cross-talk corrections. Alternatively, the channel ganging could be performed immediately after the detector primary speed/afterglow correction to achieve the maximum speed advantage. The above described processing preferably is carried out prior to the Air-cal correction (i.e., prior to normalization, channel expansion, Qcal, theta fix, and cross-talk correction).

Due to channel ganging, many of the calibration vectors applied after the Air-cal correction need to be modified to reflect the fact that each new channel now represents two of the previous channels. The affected vectors are, for example, beam hardening vectors. For the three beam hardening vectors, $B^1$, $B^2$, and $B^3$, the following relationships are used to generate new vectors:

$$B'^1_k = 0.5(B^1_{2k} + B^1_{2k+1})$$
$$B'^2_k = 0.5(B^2_{2k} + B^2_{2k+1})$$
$$B'^3_k = 0.5(B^3_{2k} + B^3_{2k+1}) \quad (5)$$

Since the vectors are generated prior to the "recon-loop", modification to the vector generation process should not affect the reconstruction performance in terms of speed.

One direct impact of the double channel ganging on the image quality is reduced spatial resolution. For example, the smallest object that a CT fluoro system needs to resolve is 5 mm. To at least partially compensate for the loss of resolution, a reconstruction filter kernel boost can be utilized. Particularly, the reconstruction filter (in frequency domain) is multiplied by a window function which has a higher magnitude in the mid to high frequency range, such as the following window function:

$$\omega = 1 + \alpha_1 f + \alpha_2 f^2 + \alpha_3 f^3 + \alpha_4 f^4 \quad (3)$$

where $\alpha_1$ to $\alpha_4$ are parameters. In one specific embodiment, the parameter set of $\alpha_1 = 0.0$, $\alpha_2 = 0.6$, $\alpha_3 = 0.2$, and $\alpha_4 = 0.0$ is utilized.

The above described filter kernel boost can also be applied to other situations where system resolution needs to be improved due to other factors. For example, reconstruction kernel boost can be utilized to compensate for the degradation of resolution due to the removal of a frequency domain interpolation process. Particularly, the projection data after the Fourier transform is replicated before being multiplied by the filter kernel. This process equals performing the interpolation in frequency space, since the filtered projection after this process will be doubled in terms of the number of sampling points. Since the interpolation is performed in frequency space, it preserves the frequency contents in the projection. This process, however, is computationally expensive, since it increase the size of the Fourier transform by a factor of 2. For reconstruction speed, it may be desirable to perform the interpolation in the spatial domain. For example, a 4-point Lagrange interpolator can be used. However, a slight degradation in system resolution will result. This can be compensated for by pre-multiplying the filter kernel by a window function (Equation 3). For the standard and soft reconstruction kernels, the parameter set $\alpha_1 = 0.0$, $\alpha_2 = 0.1$, $\alpha_3 = 0.3$, and $\alpha_4 = 0.0$ can be utilized.

C. Filtering

To reduce patient motion artifacts, the weighting scheme described below can be utilized to minimize the amount of filtering performed on each view. Particularly, for CT fluoroscopy applications, and in an exemplary implementation, images are generated at 6 frames per second with the gantry rotating about the patient one revolution per second. Therefore, highly overlapped reconstruction is performed. In other words, each projection is used in the generation of multiple images. Since the filtering process is the most time consuming portion of the reconstruction, it is desirable to avoid repeatedly filtering each projection for each reconstructed image.

Accordingly, an overscan weighting algorithm can be utilized. Since the overscan weight is constant along the channel direction, the filtering operation and weighting operation can be reversed and only one filtering per projection is needed. Each filtered projection can then be multiplied by different weights prior to the backprojection. The overscan weighting algorithm is performed in accordance with the following.

$$\omega(\gamma, \beta) = 3\theta^2(\gamma, \beta) - 2\theta^3(\gamma, \beta) \quad (4)$$

where $$\theta(\gamma, \beta) = \begin{cases} \dfrac{\beta}{\beta_o} & 0 \leq \beta < \beta_o \\ 1 & \beta_o \leq \beta < 2\pi \\ \dfrac{2\pi + \beta_o - \beta}{\beta_o} & 2\pi \leq \beta < 2\pi + \beta_o \end{cases}$$

where $\beta_o$ is a parameter which specifies the overscan angle. The parameter $\beta_o$ is determined based on the best compromise between image quality and reconstruction speed.

The above described weighting de-emphasizes the contributions from the start and end of the scan. For each view, the tomographic reconstruction filter is applied first, followed by multiplying the views by at least two different weights, then followed by backprojecting the weighted views to at least two different image locations. The content of each image memory is then transferred and initialized after a pre-determined number of views are accumulated.

Figure 4:
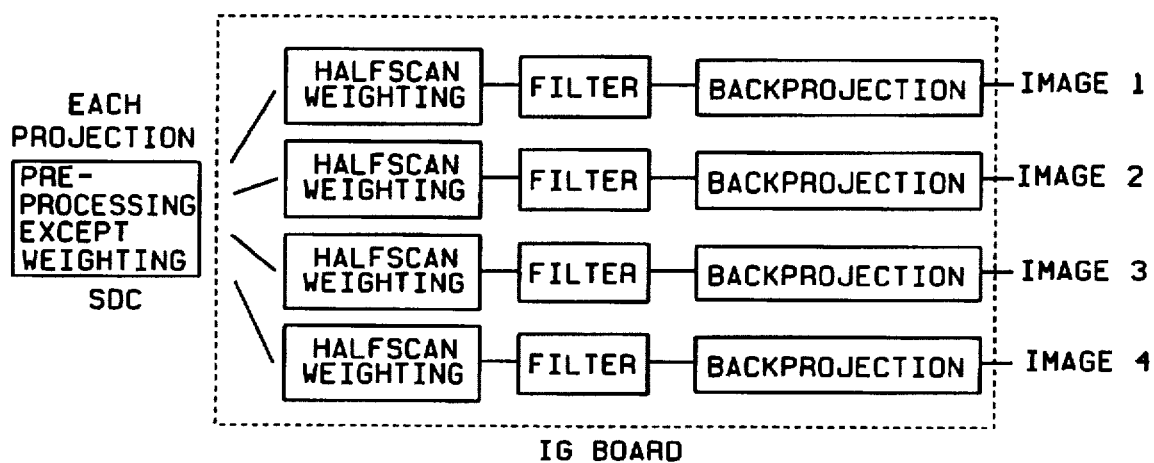
FIG. 4 is a schematic illustration of an exemplary image generation board.

In addition, halfscan weights with multiple processors to perform multiple filtering can also be utilized. Particularly, assume that at a given image frame rate, each projection contributes to N images at most. For example, N=2 for 3 frame/rotation and N=4 for 5 frame/rotation. The data processing architecture illustrated in FIG. 4 can be used for simultaneous multiple images reconstruction. Segmented reconstruction is utilized for the best temporal resolution. Also, only two branches are needed for 3 frame/rotation. The bottleneck of the architecture is the filtering step, which can be sped up by eliminating Fourier domain interpolation, and 2:1 channel compression.

A faster frame rate can be achieved by adding a second image generation board. Also, some preprocessing and postprocessing steps can be bypassed to further speed up the data processing.

D. Backprojection

In the CT Fluoro mode, since six different images are under reconstruction at any time, the multiple weighted projections needed for these images are loaded into the backprojector memory at one time. Based on the selected overscan angle, the number of weighted projections can be reduced to speed-up the data transfer to the backprojector memory. More particularly, and in an exemplary system, for every ⅙th of the overscan rotation, a complete image is generated at one location. The backprojector memory therefore is divided into 6 sub-regions. At each time instance, a filtered projection is weighted with different overscan weights and backprojected into all six sub-regions. In one specific implementation, for example, 696 views are required to generate a complete image. Therefore, after the 696th projection is backprojected, the first complete image is pulled from sub-region number 1. 116 views later, a second complete image is pulled from the sub-region number 2. The process repeats after the completion of the 6th image.

In the exemplary system, the reconstruction board is divided into 8 parallel pipes and since 6 images/overscan rotations are generated, the number of views used for each image generation needs to be divisible by 48 (i.e., 6 times 8). The above described selection is not divisible by 48 (i.e., 696 is not divisible by 48). It is undesirable, of course, to significantly increase the overscan angle (e.g., the smallest number larger than 696 and divisible by 48 is 720, which corresponds to an overscan angle of 35.1 degree), because lag will be significantly increased. It also is undesirable to significantly reduce the overscan angle (e.g., the largest number smaller than 696 and divisible by 48 is 672, which corresponds to an overscan angle of 8.8 degrees), because patient motion artifacts will significantly increase.

Accordingly, and to increase the speed of backprojection, and rather than starting each image at the multiple of 116 views, the second image is started at view 120. The third image starts 112 views after the second image. The fourth image starts again 120 views later. The fifth image is further delayed by 112 views. This process continuous.

More generally, let N denote the number of views required to generate a complete image. Also, let X denote the number of parallel processing pipes, and Y denote the number of images generated per N-view-rotation. If N is divisible by Y and not divisible by (XY), the starting view number for the consecutive images can be alternated at (N/Y)+X/2 and (N/Y)−X/2 views after the starting view of the previous image. The order is interchangeable.

The above described backprojection algorithm avoids significant penalties on system delay and image artifacts. There is, of course, a very slight non-uniform time interval between images, which varies by a few milli-seconds. Further, if the backprojector has sufficient speed, each projection can be backprojected a number of times, e.g., 6 times. The backprojected view can then be scaled and added to different image memories.

Figure 5:
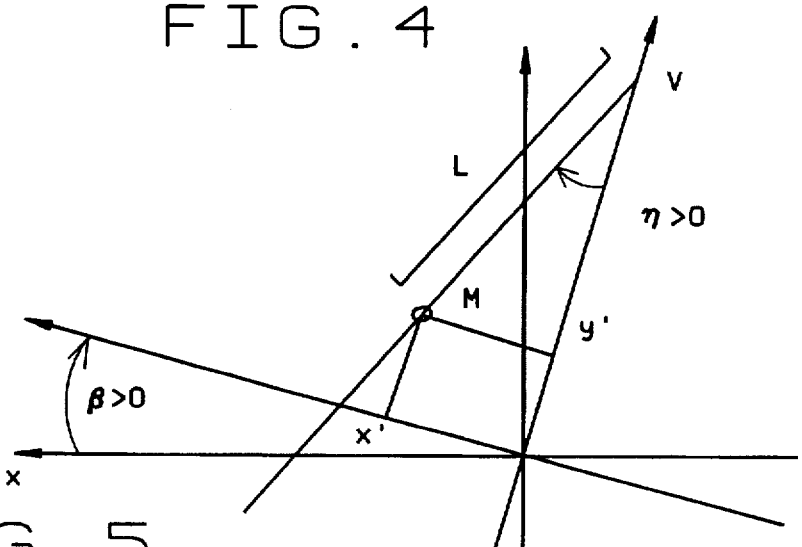
FIG. 5 illustrates a fan-beam projection for a view angle $\beta$.

In addition, a simplified backprojection technique can be used under the conditions where backprojection is the bottle neck of the reconstruction process. More particularly, the basic image backprojection operations are as follows. Each filtered projection is backprojected onto the image through a loop over the reconstruction grid pixels. Considering the patient coordinate system (x,y) and the rotated coordinate system (x',y') associated with the current view (FIG. 5) the backprojection relies on a calculation of the fan angle $\eta$ (view and pixel dependent), to perform an interpolation of the appropriate projection data. Back projection also requires calculation of $(1/L)^2$, where $L=L(\beta,x,y)$ is the pixel to fan-vertex distance (view and pixel dependent). By linearizing $\eta$ and $(1/L)^2$ around $\beta_0$ and $(x_o, y_o)$, then:

$$\eta(\beta_o + d\beta) \approx \eta(\beta_o) + A \times d\beta \qquad (10)$$

$$\frac{1}{L^2(\beta_o + d\beta)} \approx \frac{1}{L^2(\beta_o)} + B \times d\beta \qquad (11)$$

In the view-to-view only linearization application, a full calculation of the quantities $\eta$ and $(1/L)^2$ takes place every M views, where M is a parameter. For each other view, the quantities are estimated using linear interpolation. In practice, it is simpler to calculate the linear approximation by relying on a pre-calculation of the next view to be fully processed. In the view-to-view and within view linearization, the method the same method described above except that for those views which were previously fully processed, calculation for $\eta$ and $(1/L)^2$ occurs only once every P pixels, and the values in between are linearly interpolated.

The backprojection equations are:

$$\hat{x} = \frac{x'}{S}; \quad \hat{y} = \frac{y'}{S} \qquad (12)$$

$$\tan\eta = \frac{x'}{S-y'} = \frac{\hat{x}}{1-\hat{y}}; \quad \text{Let } U = \frac{1}{1-\hat{y}};$$

$$\eta = a\tan(\hat{x} \times U); \quad \left(\frac{1}{L}\right)^2 = \left(\frac{S}{L \times \cos\eta}\right)^2 = U^2$$

These relationships serve as the basic relationship from which the fan angle and the inverse-squared of the distance from the fan-vertex to the pixel are determined. Simplifying these relationships provides significant computational savings. In particular, in the view-to-view linearization approach, the following relationships apply:

$$\eta(\beta_0 + d\beta) \approx \eta(\beta_0) + A \times d\beta \qquad (13)$$

$$A = \frac{S^2}{L^2}[\hat{y}(1-\hat{y}) + \hat{x}] \qquad (14)$$

and:

$$\frac{1}{L^2(\beta_0 + d\beta)} \approx \frac{1}{L^2(\beta_0)} + D \times d\beta \qquad (15)$$

$$D = \frac{-2\hat{x}}{L^3(\beta_0)} \qquad (16)$$

Parameters A and D do not have to be determined using equations (14) and (16). Instead, A and D may be estimated from a "look-ahead" full calculation for views N and N+M. For the views in the interval ]N,N+M[, calculations in equation (12) are skipped and replaced by a linear approximation based on estimating A and D from views N and N+M.

E. Parallel Processing

To further speed-up the reconstruction process, it is contemplated that many processes can be performed on different processors in parallel. For example, the pre-processing, filtering, backprojection, and post-processing can each be performed on different processors. With such a configuration, and while one processor is processing view i, a different processor can process view i+1. Further, while the backprojector is processing image number i, the post-processing unit can process image number i−1.

The above described CT Fluoro system has an increased frame rate as compared to known fluoro system yet provides acceptable image quality. Of course, the system can implement only selected ones of the above described algorithms and a selected combination of such algorithms, and does not necessarily implement all the algorithms.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

We claim:

1. A computed tomography system comprising an x-ray source, an x-ray detector aligned with said x-ray source, said x-ray detector comprising a plurality of detector cells, and a processor coupled to said x-ray detector, said system configured to obtain a first set of projection data from a scan, said processor configured to:

compress said first set of data by combining multiple views into one view and maintain a constant view angle increment between compressed views;

generate a second set of data using interpolation;

gang projection data from at least two adjacent detector cells;

at least partially compensate for loss of resolution;

select respective views at which each respective image is to be generated, said views selected based on a number N of views required to generate a complete image, a number X of parallel processing pipes, and a number Y of images generated per N-view-rotation; and perform a backprojection wherein quantities used in the backprojection are based on linearization from view to view.

2. A computed tomography system in accordance with claim 1 wherein said compressed data set is generated in accordance with:

$$P_{compressed}(k) = \begin{cases} P_{original}\left(\dfrac{3k}{2}\right) & k = 0, 2, 4, \ldots \\ 0.5\left[P_{original}\left(\dfrac{3k-1}{2}\right) + P_{original}\left(\dfrac{3k+1}{2}\right)\right] & k = 1, 3, 5, \ldots \end{cases}$$

3. A computed tomography system in accordance with claim 1 wherein said second set of data is generated for a set of gantry angles which bisect gantry angles of said first set of data.

4. A computed tomography system in accordance with claim 1 wherein said ganging is performed in accordance with:

$$\xi'_k = \xi_{2k} + \xi_{2k+1}.$$

5. A computed tomography system in accordance with claim 4 wherein said processor is further configured to transform beam hardening vectors $B^1$, $B^2$, and $B^3$ to generate vectors:

$$B'^1_k = 0.5(B^1_{2k} + B^1_{2k+1})$$

$$B'^2_k = 0.5(B^2_{2k} + B^2_{2k+1})$$

$$B'^3_k = 0.5(B^3_{2k} + B^3_{2k+1}).$$

6. A computed tomography system in accordance with claim 1 wherein to at least partially compensate for loss of resolution, said processor is configured to multiply a reconstruction filter by a window function having a higher magnitude.

7. A computed tomography system in accordance with claim 6 wherein said window function is:

$$\omega = 1 + \alpha_1 f + \alpha_2 f^2 + \alpha_3 f^3 + \alpha_4 f^4$$

where $\alpha_1$ to $\alpha_4$ are parameters.

8. A computed tomography system in accordance with claim 7 wherein $\alpha_1=0.0$, $\alpha_2=0.6$, $\alpha_3=0.2$, and $\alpha_4=0.0$.

9. A computed tomography system in accordance with claim 1 wherein said processor is further configured to weight said data.

10. A computed tomography system in accordance with claim 9 wherein said weighting is performed in accordance with:

$$\omega(\gamma,\beta) = 3\theta^2(\gamma,\beta) - 2\theta^3(\gamma,\beta)$$

where:

$$\theta(\gamma, \beta) = \begin{cases} \dfrac{\beta}{\beta_o} & 0 \leq \beta < \beta_o \\ 1 & \beta_o \leq \beta < 2\pi \\ \dfrac{2\pi + \beta_o - \beta}{\beta_o} & 2\pi \leq \beta < 2\pi + \beta_o \end{cases}$$

where $\beta_0$ is a parameter which specifies the overscan angle.

11. A computed tomography system in accordance with claim 1 wherein to select respective views at which each respective image is to be generated, and if N is divisible by Y and not divisible by (XY), said processor is further configured to alternate as a starting view number for consecutive images (N/Y)+X/2 and (N/Y)−X/2 views.

12. A computed tomography system in accordance with claim 1 wherein $\eta$ and $(1/L)^2$ are linearize around $\beta_0$ and $(x_0, y_0)$, and:

$$\eta(\beta_o + d\beta) \approx \eta(\beta_o) + A \times d\beta$$

$$\dfrac{1}{L^2(\beta_o + d\beta)} \approx \dfrac{1}{L^2(\beta_o)} + B \times d\beta.$$

13. A computed tomography system in accordance with claim 12 wherein a full calculation of $\eta$ and $(1/L)^2$ takes place every M views, where M is a parameter, and wherein for each other view, the quantities are estimated using linear interpolation.

14. A computed tomography system in accordance with claim 13 wherein a calculation for $\eta$ and $(1/L)^2$ is performed once every P pixels, and values between said calculated values are linearly interpolated, and wherein the backprojection equations are:

$$\hat{x} = \dfrac{x'}{S}; \quad \hat{y} = \dfrac{y'}{S}$$

$$\tan\eta = \dfrac{x'}{S - y'} = \dfrac{\hat{x}}{1 - \hat{y}}; \quad \text{Let } U = \dfrac{1}{1 - \hat{y}}:$$

$$\eta = a\tan(\hat{x} \times U); \quad \left(\frac{1}{L}\right)^2 = \left(\frac{S}{L \times \cos\eta}\right)^2 = U^2.$$

15. A computed tomography system in accordance with claim 14 wherein:

$$\eta(\beta_0 + d\beta) \approx \eta(\beta_0) + A \times d\beta$$

$$A = \frac{S^2}{L^2}[\hat{y}(1-\hat{y}) + \hat{x}]$$

and:

$$\frac{1}{L^2(\beta_0 + d\beta)} \approx \frac{1}{L^2(\beta_0)} + D \times d\beta$$

$$D = \frac{-2\hat{x}}{L^3(\beta_0)}.$$

16. A computed tomography system in accordance with claim 1 further comprising multiple processors for performing parallel processing.

17. A computed tomography system in accordance with claim 16 wherein multiple images are generated by said multiple processors.

18. A computed tomography system in accordance with claim 16 wherein one image is generated at one time by said multiple processors.

19. A computed tomography system comprising an x-ray source, an x-ray detector aligned with said x-ray source, said x-ray detector comprising a plurality of detector cells, and a processor coupled to said x-ray detector, said system configured to obtain a first set of projection data from a scan, said processor configured to at least partially compensate for loss of resolution by multiplying a reconstruction filter by a window function having a higher magnitude.

20. A computed tomography system in accordance with claim 19 wherein said window function is:

$$\omega = 1 + \alpha_1 f + \alpha_2 f^2 + \alpha_3 f^3 + \alpha_4 f^4$$

where $\alpha_1$ to $\alpha_4$ are parameters.

21. A computed tomography system in accordance with claim 20 wherein $\alpha_1 = 0.0$, $\alpha_2 = 0.6$, $\alpha_3 = 0.2$, and $\alpha_4 = 0.0$.

22. A computed tomography system comprising an x-ray source, an x-ray detector aligned with said x-ray source, said x-ray detector comprising a plurality of detector cells, and a processor coupled to said x-ray detector, said system configured to linearize $\eta$ and $(1/L)^2$ around $\beta_0$ and $(x_0, y_0)$, and:

$$\eta(\beta_o + d\beta) \approx \eta(\beta_o) + A \times d\beta$$

$$\frac{1}{L^2(\beta_o + d\beta)} \approx \frac{1}{L^2(\beta_o)} + B \times d\beta.$$

23. A computed tomography system in accordance with claim 22 wherein a full calculation of $\eta$ and $(1/L)^2$ takes place every M views, where M is a parameter, and wherein for each other view, the quantities are estimated using linear interpolation.

24. A computed tomography system in accordance with claim 23 wherein a calculation for $\eta$ and $(1/L)^2$ is performed once every P pixels, and values between said calculated values are linearly interpolated, and wherein the backprojection equations are:

$$\hat{x} = \frac{x'}{S}; \quad \hat{y} = \frac{y'}{S}$$

$$\tan\eta = \frac{x'}{S - y'} = \frac{\hat{x}}{1 - \hat{y}}; \quad \text{Let } U = \frac{1}{1 - \hat{y}}:$$

$$\eta = a\tan(\hat{x} \times U); \quad \left(\frac{1}{L}\right)^2 = \left(\frac{S}{L \times \cos\eta}\right)^2 = U^2.$$

25. A computed tomography system in accordance with claim 24 wherein:

$$\eta(\beta_0 + d\beta) \approx \eta(\beta_0) + A \times d\beta$$

$$A = \frac{S^2}{L^2}[\hat{y}(1-\hat{y}) + \hat{x}]$$

and:

$$\frac{1}{L^2(\beta_0 + d\beta)} \approx \frac{1}{L^2(\beta_0)} + D \times d\beta$$

$$D = \frac{-2\hat{x}}{L^3(\beta_0)}.$$

* * * * *